United States Patent [19]

Rangaswamy

[11] Patent Number: 4,568,326
[45] Date of Patent: Feb. 4, 1986

[54] EPISTAXIS SPONGE

[76] Inventor: Avvari Rangaswamy, P.O. Box 426, 13 Eastern Dr., Littleton, N.C. 27850

[21] Appl. No.: 603,832

[22] Filed: Apr. 25, 1984

Related U.S. Application Data

[63] Continuation-in-part of Ser. No. 343,234, Jan. 27, 1982, abandoned.

[51] Int. Cl.⁴ .................... A61M 35/00; A61B 17/12
[52] U.S. Cl. .......................................... 604/1; 128/342
[58] Field of Search ................... 604/1, 2, 3, 890, 285, 604/286; 128/325, 342

[56] References Cited

U.S. PATENT DOCUMENTS

| | | | |
|---|---|---|---|
| 982,232 | 1/1911 | Bartholomew | 604/1 |
| 1,629,436 | 5/1927 | Capri | 604/1 |
| 2,362,704 | 11/1944 | McGivern | 604/1 |
| 2,490,168 | 12/1949 | Strauss | 604/1 |
| 4,338,941 | 7/1982 | Payton | 128/342 |
| 4,457,756 | 7/1984 | Kern et al. | 128/342 |

Primary Examiner—C. Fred Rosenbaum
Assistant Examiner—Michelle N. Lester
Attorney, Agent, or Firm—Memel, Jacobs, Pierno, Gersch and Ellsworth

[57] ABSTRACT

An article to be used as an aid in the treatment of epistaxis consisting of a fluid absorbing portion which is pear shaped in cross-section for insertion into a part of the nasal cavity with a semi-rigid handle portion having along one end section a multi-spoked support structure about which the fluid absorbing portion is mounted and maintained in the pear shaped cross section. When inserted into the nasal cavity the pear shaped cross section of the fluid absorbing portion, as maintained by the support structure, provides both essentially uniform pressure for constricting blood flow and localities for aggregation of fibrin to promote blood clotting.

7 Claims, 3 Drawing Figures

EPISTAXIS SPONGE

This application is a continuation-in-part application of co-pending application Ser. No. 343,234, filed Jan. 27, 1982, now abandoned.

BACKGROUND OF THE INVENTION

Epistaxis, i.e., nose bleeding, while quite common and generally experienced by everyone at one time or another is at best an inconvenient and often disturbing experience. Even though considerable advances have been achieved in the treatment of a wide variety of disorders, the time honored methods for controlling anterior nose bleeding remains relatively unimproved. Simply tilting the head back, using cold compresses, squeezing the anterior part of the nose, i.e., the septum, and finally packing the nasal cavity are employed as standard epistaxis inhibiting techniques. The drawbacks to these techniques are personally known to almost everyone and in particular the discomfort of squeezing the nose with the resultant need for breathing through the mouth. In the case of packing, there is a need for special instruments and professional expertise when both packing and unpacking the nasal cavity.

Nose bleeds can occur for a wide variety of reasons including rheumatic fever, infectious mononucleosis, sickle cell anemia, systemic haemorrhagic disorders and hypertension (in adults), hemagiomas, hereditary telangiectasis and angiofibromas. The most common cause of expistaxis in children arise from excessive drying, which can be traumatized by such activities as nose picking. The most common location for such varicosities is on the nasal septum above the nasal floor and approximately 0.5 cm inside the nose. This is characterized as Kiesselbauch's area and is the anastomotic site for a number of arterioles. Traumatizing a varicosity in this area sufficiently to produce epistaxis is commonly referred to as an anterior nose bleed.

SUMMARY OF THE INVENTION

A shaped, semi-rigid and absorbent device is provided by the present invention. This device is adapted to be easily inserted and removed from the nasal cavity. Such a shaped device is by virtue of its structure capable of absorbing blood while providing pressure on the traumatized mucosa, which will tend to inhibit further bleeding.

The shaped fluid absorbent portion of the present invention is mounted from a stem having a handle structure located at the other end which can be held for facilitating insertion and withdrawal of the absorbent portion of the device from the nasal cavity. Additionally, attached to the stem is a support structure which is so constructed as to provide a framework for maintaining a preselected shape for the absorbent material attached to the device. This preselected shape is chosen to approximate that of the anterior nasal cavity, which is, in cross section, generally pear shaped. By using the support structure to maintain the absorbent portion in a general pear shape, when viewed in cross section with respect to the stem, the absorbent portion can be inserted into the nasal cavity and thus mimic the volume of the anterior cavity so that essentially uniform pressure can be applied to the lumen of the nasal cavity. The application of uniform pressure about the lumen of the nasal cavity induces an essentially uniform constriction of blood flow which beneficially promotes control of bleeding without localized strangulation of blood flow that would result, for example, from use of an undersized swab pressed only against the area from which bleeding is originating. Further, the closely forming absorbent portion of the present invention provides a locality for concentrating fibrin associated with clotting of blood, which, therefore, enhances formation of clots. Since the absorbent portion of the present invention essentially uniformly contacts the nasal cavity's lumen there are no large voids, such as folds in the absorbent material, where blood clots could form, and thus on extraction of the absorbent material from the nasal cavity cause further bleeding at the original location or at new locations.

BRIEF DESCRIPTION OF THE DRAWINGS

The various objects, advantages and novel features of the present invention will be more readily apprehended from the following detailed description when read in conjunction with the appended drawings, in which.

DETAILED DESCRIPTION OF THE INVENTION

Figure 1:
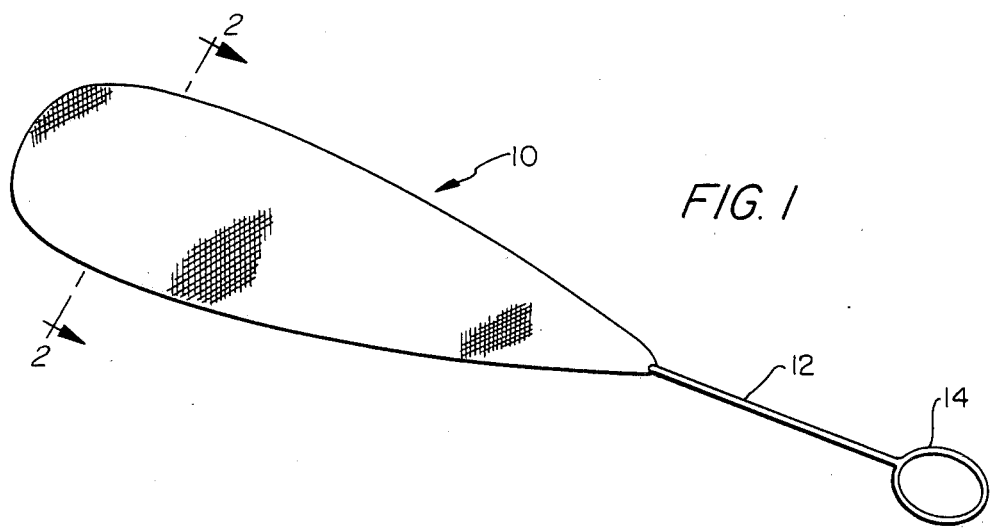
FIG. 1 is a perspective view of the device of the present invention.

The device, 10, of the present invention is characteristically constructed around a semi-rigid, flexible stem 12 which is provided with a gripping portion or handle 14 and a support system 16. The length of the stem 12 can vary as well as the specific shape of the handle 14 depending on the functional requirements and physical properties of the materials selected. Of importance are the requirements that: (1) the support system 16 provide an architecture for the absorbent material, 18, to be maintained in a preselected shape: and, (2) the stem 12 be both rigid and yet flexible enough for manipulation during insertion of the shaped absorbent material 18 into the nasal cavity and removal therefrom. The rigidity of stem 12 is important since stem 12 provides the support for the totality of the device 10. For a preferred embodiment, a flexible plastic is used to fabricate the flexible stem 12, handle 14 and support system 16.

The support system 16 radiates from the stem 12. This support system 16 includes four secondary stems 20 which branch from the stem 12 and progress longitudinally along the length of stem 12. From the stem 12 to each of the secondary stems 20 are support spokes 22. As arranged the spokes 22 and secondary stems 20 establish a sturdy but flexible architecture about which absorbent cotton 18 is packed. The absorbent cotton 18 is wrapped with at least one and preferably two layers of cotton gauze 24. The cotton gauze 24 can be impregnated with petrolatum or other suitable medication. The absorbent cotton 18 and cotton gauze 24 may also be replaced with other suitable natural or synthetically manufactured absorbent materials as long as these materials can be arranged about the support system 16 and maintained in a preselected shape. Further, the absorbent materials should preferably expand slightly when absorbing blood.

Figure 2:
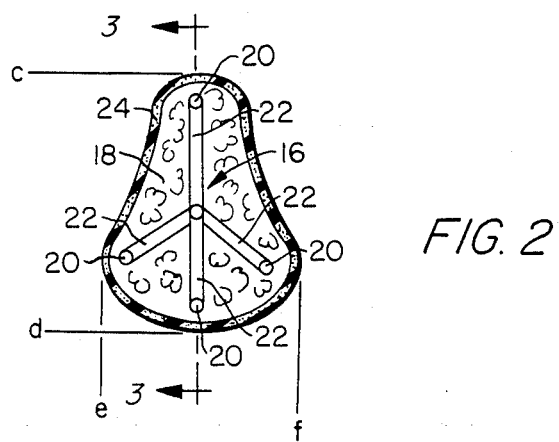
FIG. 2 is an end view of the device taken along the line 2—2 shown in FIG. 1; and, FIG. 3 is a longitudinal sectional view taken along the line 3—3 shown in FIG. 2.

It is a particularly important aspect of the present invention that the cross section and shape of the absorbent portion, see FIG. 2, be maintained as close as is practicable to the pear shape of the vestibule of the anterior nasal cavity. In general, the greatest width of the pear shape, i.e., (e-f), see FIG. 2, which is below the mid-point along the dimension (c-d), is approximately one half the height (c-d) of the device 10. The secondary stems 20 and spokes 22 are located so as to provide this dimensional relationship between (c-d) and (e-f) as described above.

Figure 3:
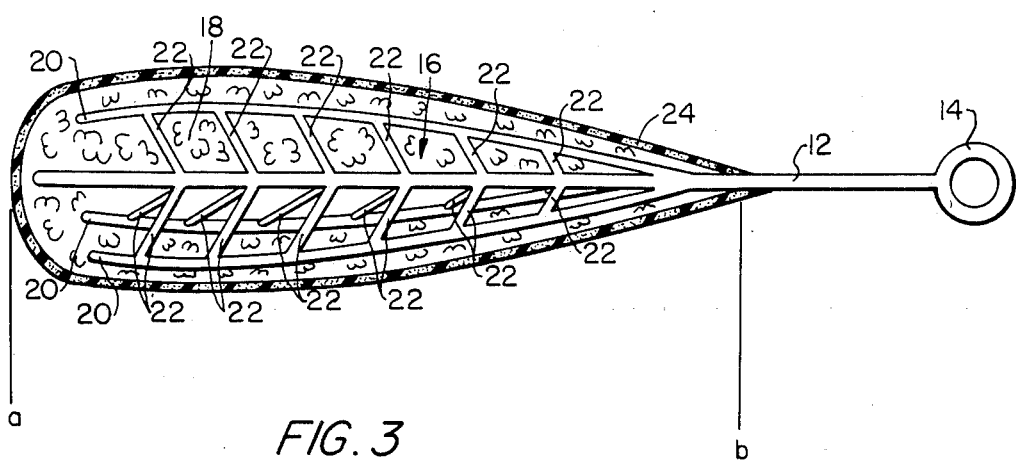

For use by adult patients the dimension (a-b), see FIG. 3, should be approximately 4 cm. Several sizes can, of course, be constructed, for example the dimension (a-b) can be 3.5 cm or 2 cm, to accommodate differences in patient anatomy. Preferable dimensions for device 10 will approximately bear the following relative relationship:

| Length (a-b) | Height (c-d) | Width (e-f) |
| --- | --- | --- |
| 4 cm | 2.5 cm | 1.25 cm |
| 3.5 cm | 2.25 cm | 1.125 cm |
| 3.0 cm | 2.0 cm | 1.0 cm |
| 2.0 cm | 1.5 cm | 0.75 cm |

The anteroposterior dimension (c-d) and the transverse dimension (e-f) are important for both adaptation and a comfortable fit for the device 10 into the nasal cavity.

The device 10 of the present invention can also be used to sponge or mop or provide control of bleeding points in the mucosa of the nasal cavity during minor surgery.

This invention has been described with reference to its current preferred embodiment. However, it will be appreciated that a wide variation in material selection is possible and other materials may be substituted to obtain the functional advantages disclosed herein. Likewise, further modifications are possible, as for example, the incorporation of soluble medicaments in the absorbent material 18 or on the surface material 24 to aid in coagulation, the prevention of infection or the like, without detracting from the function of the device, where such additives are a contemplated improvement for either a general or specialized function.

What is claimed is:

1. An epistaxis treatment device comprising a stem means, a fluid absorbing pad means affixed to one end of said stem means, and a handle means disposed at the other end of said stem means for inserting into and removing from a nasal cavity said pad means; said fluid absorbing pad means having a substantially pear shaped outer cross-section, the height of said pear shaped cross-section being about twice the maximum width thereof, and the axis of said maximum width being positioned at a location vertically spaced from the middle of the height axis; said stem means including an integral support system means which maintains the pear shaped cross-section of the pad means;

whereby insertion of said pear shaped fluid absorbing pad in a nasal cavity facilitates absorption of fluid and applies pressure on the traumatized mucosa of the nasal cavity.

2. The epistaxis treatment device as set forth in claim 1 in which said fluid absorbing pad means is affixed to said support system means, and said stem means extends beyond the end of said fluid absorbing pad means a sufficient distance to be capable of being grasped for positioning and inserting said fluid absorbing pad means in a nasal cavity thereby providing for ease of insertion of said fluid absorbing pad into the nasal cavity and subsequent removal therefrom.

3. The epistaxis treatment device as set forth in claim 1 in which a core of absorbent cotton is mounted about said support system means, and said core of absorbent cotton is surrounded by at least one layer of cotton gauze to form said fluid absorbent pad means.

4. The epistaxis treatment device as set forth in claim 1 in which said fluid absorbing means is formed from materials capable of resiliently expanding when fluid is absorbed, thereby increasing the pressure applied by said fluid absorbing pad to the nasal mucosa as fluid is absorbed.

5. The epistaxis treatment device as set forth in claim 1 in which said support system means includes four secondary stems which branch from said stem means and extend longitudinally along the length of said stem means, said secondary stems being supported along their length by spoke elements extending from said stem means.

6. A method of treating epixtaxis comprising the steps of:
(i) inserting into a nasal cavity an epistaxis treatment device comprising a stem means, a fluid absorbing pad means affixed to one end of said stem means, and a handle means disposed at the other end of said stem means; said fluid absorbing pad means having a substantially pear shaped outer cross-section; said stem means including an integral support system means which maintains the pear shaped cross-section of the pad means;
(ii) permitting coagulation to occur; and,
(iii) removing said fluid absorbing pad by grasping said handle means and withdrawing said fluid absorbing pad from said nasal cavity.

7. The method of treating epistaxis as set forth in claim 6 in which medicaments are introduced into the nasal cavity by said fluid absorbing pad.

* * * * *